United States Patent [19]
Christensson

[11] Patent Number: 5,944,562
[45] Date of Patent: *Aug. 31, 1999

[54] CLASP STRUCTURE FOR BIOMEDICAL ELECTRODES

[76] Inventor: Eddy K. G. Christensson, 4016 Inglewood Ave. S., Edina, Minn. 55416

[ * ] Notice: This patent is subject to a terminal disclaimer.

[21] Appl. No.: 08/848,593

[22] Filed: Apr. 28, 1997

Related U.S. Application Data

[63] Continuation-in-part of application No. 08/355,954, Dec. 14, 1994, Pat. No. 5,624,281.

[51] Int. Cl.$^6$ ........................................ H01R 4/48
[52] U.S. Cl. ..................... 439/729; 439/909; 439/261; 439/859; 607/152
[58] Field of Search .................................. 439/729, 859, 439/854, 259, 261, 909, 465, 456, 332, 337, 445, 764, 933, 781, 863, 864, 338, 342, 374

[56] References Cited

U.S. PATENT DOCUMENTS

| | | | |
|---|---|---|---|
| D. 251,387 | 3/1979 | Ramsay et al. | D24/29 |
| 2,465,722 | 3/1949 | Hamilton | 173/273 |
| 3,090,029 | 5/1963 | Stroebel | 339/255 |
| 3,456,181 | 7/1969 | Godshalk | 320/25 |
| 3,543,760 | 12/1970 | Bolduc | 128/416 |
| 3,624,590 | 11/1971 | Bolduc | 339/75 R |
| 3,642,008 | 2/1972 | Bolduc | 128/416 |
| 3,671,924 | 6/1972 | Nagano | 339/95 D |
| 3,694,791 | 9/1972 | Urban | 339/75 T |
| 3,699,968 | 10/1972 | Bolduc | 128/303.13 |
| 3,810,075 | 5/1974 | Turner | 439/465 |
| 3,817,253 | 6/1974 | Gonser | 128/418 |
| 3,824,529 | 7/1974 | Dorrell | 339/99 |
| 3,842,394 | 10/1974 | Bolduc | 339/75 R |
| 3,868,165 | 2/1975 | Gonser | 339/97 R |
| 3,895,635 | 7/1975 | Justus et al. | 439/909 |
| 3,914,007 | 10/1975 | Seidler | 339/255 P |
| 4,026,278 | 5/1977 | Ricketts et al. | 439/859 |
| 4,040,697 | 8/1977 | Ramsay et al. | 339/61 R |
| 4,061,408 | 12/1977 | Bast et al. | 339/75 R |
| 4,151,462 | 4/1979 | Texler | 324/72.5 |
| 4,365,634 | 12/1982 | Bare et al. | 128/640 |
| 4,449,772 | 5/1984 | Johnson, III | 339/29 B |
| 4,453,791 | 6/1984 | Ledbetter | 339/29 B |
| 4,555,155 | 11/1985 | Drake | 339/61 R |

(List continued on next page.)

FOREIGN PATENT DOCUMENTS 1073056  1/1960  Germany ................................. 21/22

OTHER PUBLICATIONS

Commercial Product: EKG clip marketed by Hirschman of America, Riverdale, New Jersey.
Commercial Product: "Astro–Trace" Clip marketed by LeBlanc Corporation, Augusta, Georgia.
Commercial Product: EKG clip marketed by Trono Med, Inc., Irvine, California.
Commercial Product: EKG clip marketed by 3M Company, St. Paul, Minnesota.

*Primary Examiner*—Paula Bradley
*Assistant Examiner*—Alexander Gilman
*Attorney, Agent, or Firm*—James V. Harmon

[57] ABSTRACT

A clasp for a biomedical electrode includes opposed cooperating jaw members. The jaw members can be end portions of a U-shaped leaf spring. A lever is pivotally mounted for engagement with the jaws for forcing the jaws together to grip an electrode placed between them. An opening is provided within the clasp for receiving the stud of a different style electrode and an electrical contact is provided for establishing an electrical connection with the stud. Longitudinally distributed lug secure upper and lower portions of the clasp together. A telescoping connector at the free end of a lead wire removably secures the lead wire to the clasp and is rotated after insertion to lock the lead wire in place. An electrically conductive, optionally non-metallic, x-ray transparent plastic contact is described for establishing an electrical connection between a biomedical electrode and the lead wire.

17 Claims, 12 Drawing Sheets

U.S. PATENT DOCUMENTS

| | | | |
|---|---|---|---|
| 4,640,563 | 2/1987 | LeBlanc | 339/32 M |
| 4,647,131 | 3/1987 | Van Woensel | 339/74 R |
| 4,685,886 | 8/1987 | Donlinger et al. | 439/55 |
| 4,702,256 | 10/1987 | Robinson et al. | 128/639 |
| 4,761,143 | 8/1988 | Owens et al. | 439/372 |
| 4,795,857 | 1/1989 | McInnis | 439/731 |
| 4,797,125 | 1/1989 | Malana | 439/729 |
| 4,842,558 | 6/1989 | Strand | 439/558 |
| 5,295,872 | 3/1994 | Christensson | 439/822 |
| 5,407,368 | 4/1995 | Strand et al. | 439/729 |

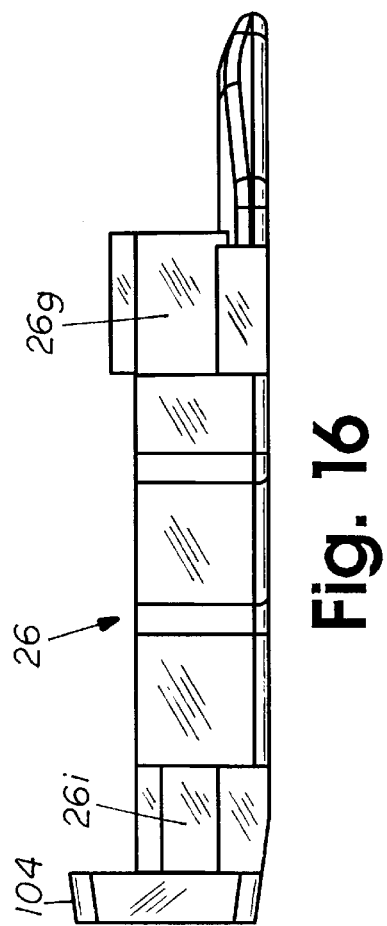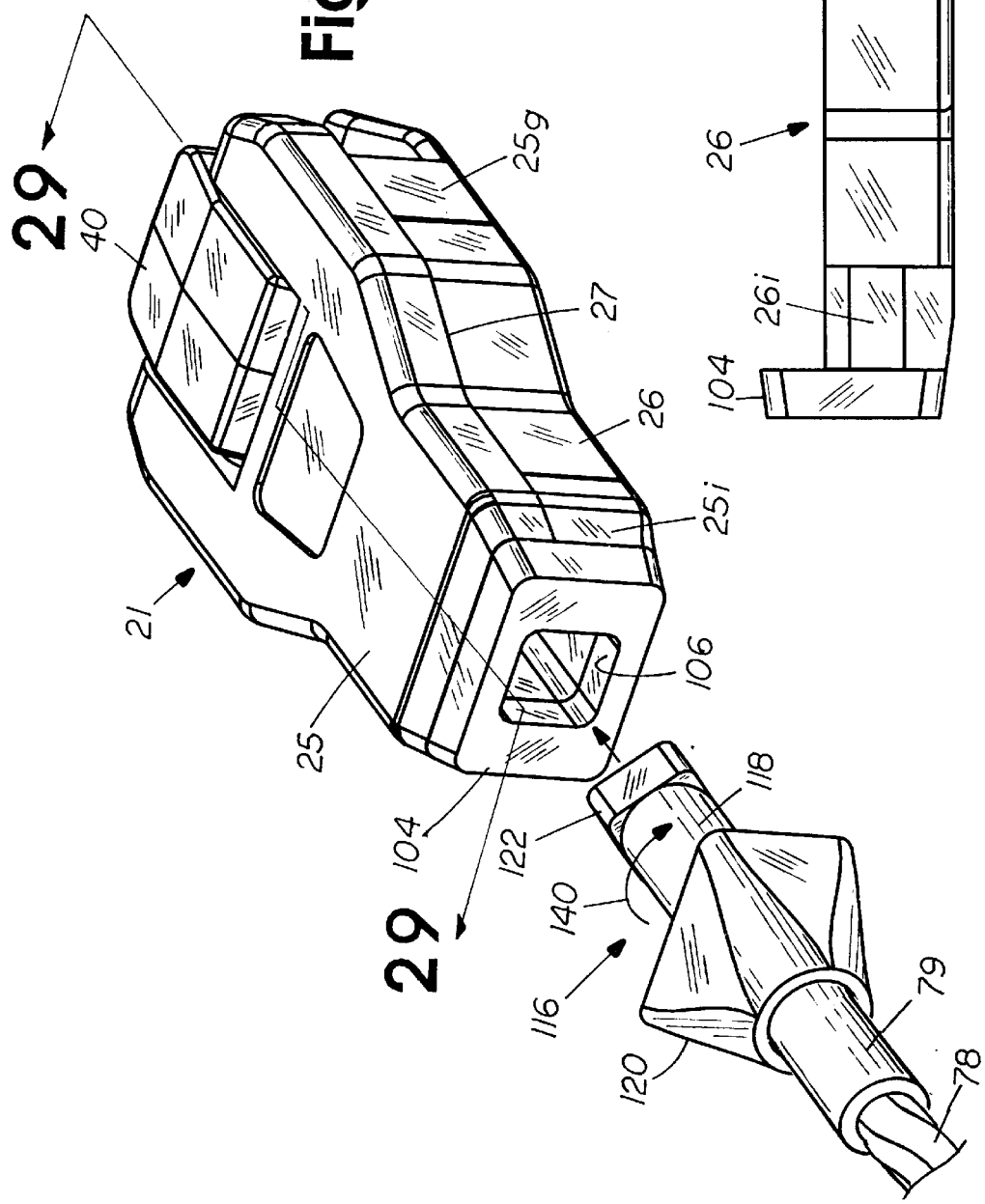

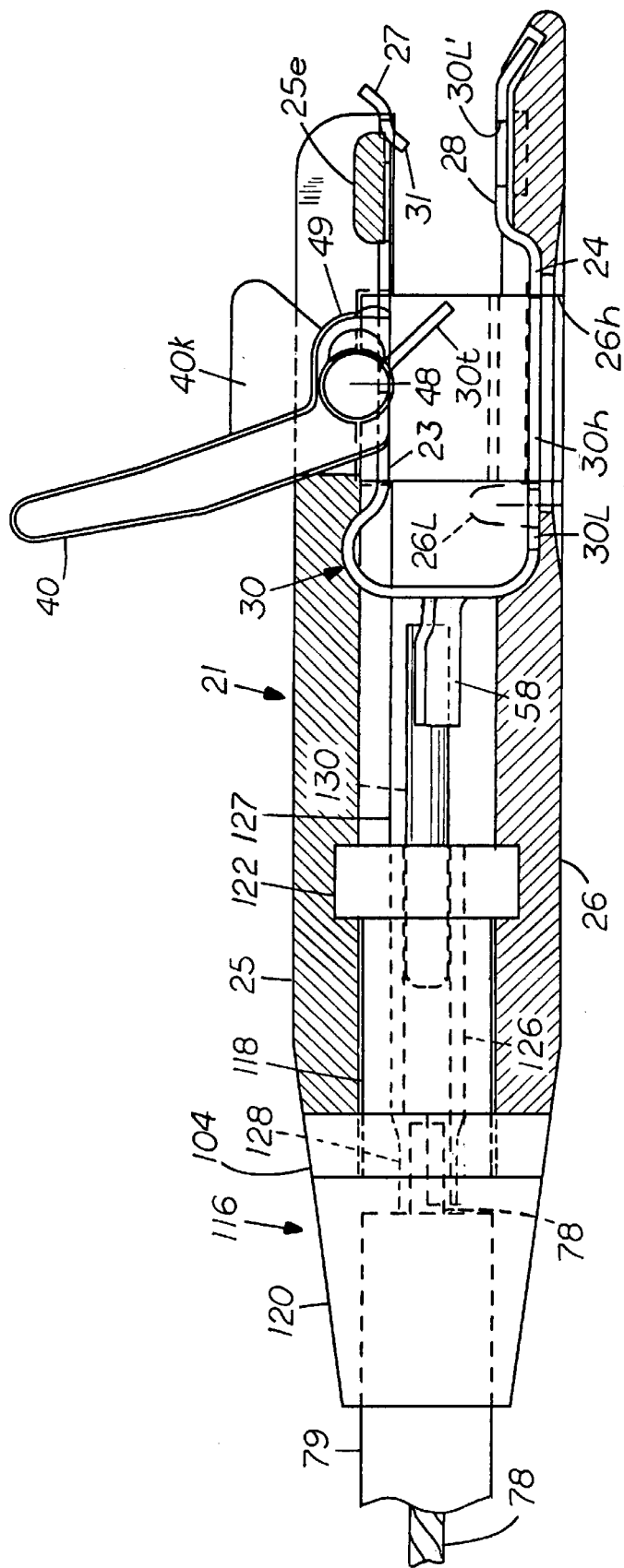
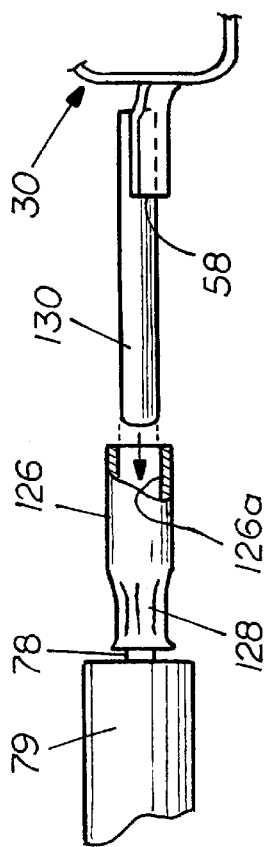
Fig. 30
Fig. 31

CLASP STRUCTURE FOR BIOMEDICAL ELECTRODES

This is a continuation-in-part of application Ser. No. 08/355,954 filed Dec. 14, 1994, now U.S. Pat. No. 5,624,281, and bearing the same title.

FIELD OF THE INVENTION

This invention relates to improved electrical clasp structures for transferring biomedical electrical signals.

BACKGROUND OF THE INVENTION

This invention is concerned with a biomedical clasp structure and especially, although not exclusively, with one capable of universal use, i.e., use with both kinds of external skin contacting electrode sensors (tab and snap types) now in use for substantially interference-free transfer of body or cardiovascular (CV) signals to electrocardiographic equipment for making ECG measurements, producing displays or for providing electrical stimulation to the body of a patient.

Disposable external electrode sensors for ECG readings are placed in contact with a patient at selected locations about the torso and limbs. These sensors are held adhesively to the skin surface and include a conductive gel or membrane that chemically reduces the resistance presented by the skin and thereby promotes the transmission of CV electrical impulses from the body of the patient via the electrodes to the associated detecting means. Two types of external disposable electrode sensors are in general use. The selection of either type is dependent on measuring conditions. One type used with the patient in a prone position for short-term measurements is a thin sheet form of electrode with an exposed planar tab for transferring sensed electrical signals. An alligator clip with jagged-edge gripping means has typically been used on an exposed planar contact tab. Another type of electrode generally used for longer-term measurements, for example, when the patient is exercising and/or being monitored for prolonged time periods, has a central metallic contact such as a male lug or nut.

As seen in FIG. 3 of U.S. Pat. No. 4,640,563 to LeBlanc, a prior art alligator clip includes jagged edge jaws at its working end and a handle for opening the jaws. As a part of the prior art connector structure, a lead wire is electrically connected by solder to one arm of the alligator clip. At the opposite longitudinal end of the lead wire, a female receptacle is provided for receiving a male member for electrical connection to the measuring equipment.

However, such an alligator clip has certain disadvantages and, in particular, cannot provide desired electrical contact and stability with a snap style contact stud. Because of the differing types of sensors and connectors, delays have occurred due to inferior and/or loose connections resulting in much frustration for the EKG operator since such connections can ruin the recording and prevent the machine from properly performing the test. Thus, it would require repeat tests and manual resecuring of prior art connections to the patient.

Because of the exposed lead wire, and other aspects of prior connectors, they could not be sterilized for repeated use in a sterile environment, had short-term life expectancy in non-sterile environments and, in general, did not provide optimum recovery of the low-energy-level patient signals available.

The present invention overcomes these problems and disadvantages by providing a single type of electrical clasp structure for obtaining accurate ECG measurements from the planar tab type electrode structures used for sensing patient signals, and allows for easy and rapid connection of a male connector leading to an electrical measuring and indicating device.

U.S. Pat. No. 4,061,408 describes a connector having an L-shaped lever arm. In the development of the present invention, it was found that such a lever is often awkward to use and is therefore not fully acceptable from a human engineering standpoint. In developing the present invention, it was noticed that the direction of lever rotation in U.S. Pat. No. 4,061,408 opposes the natural motion of the clasp itself as it is attached and later disconnected from the electrode. In addition, the patented clasp is only suited for the tab type of planar electrode. One important objective of the present invention is to overcome these deficiencies.

In contrast to the prior art, the present invention is well adapted for use with both the planar tab-type external electrode and the snap-type electrode in any type of patient monitoring or stimulation environment. It also provides a streamlined configuration. The structure can also be usefully employed, as well, in any so-called tab TENS (muscle stimulating electrode) environment and with other stimulation electrodes.

In addition, as specifically described in connection with FIGS. 15–31, it is a more specific object to provide a very secure, longitudinally distributed connection between upper and lower portions of the clasp housing; a secure, reliable but removable telescopic connection between the lead wire and the clasp; and an optional, non-metallic spring that is invisible to x-rays and consequently will not obscure anatomical structures that appear in x-ray films.

SUMMARY OF THE INVENTION

In order to establish electrical contact with a biomedical electrode, a preferred embodiment of the invention provides a clasp structure with a pair of jaws and a lever for closing the jaws when the lever is moved toward the end of the clasp where the jaws are located. Optionally, the clasp has a stud-receiving opening in which the stud of an electrode is held when the lever is moved to an operative position. Longitudinally distributed connectors are provided between the upper and lower portions of the clasp, a novel telescoping connector is described for removably attaching a lead wire to the clasp, and an electrically conductive non-metallic, x-ray transparent element is described for establishing electrical connection between a biomedical electrode and the lead wire that projects into the clasp.

The invention will be better understood by reference to the figures and detailed description which illustrate by way of example a few of the various forms of the invention within the scope of the claims.

THE FIGURES

FIG. 15 is a perspective view of a modified form of the invention having a removable connector for attaching a lead wire to the clasp.

FIG. 16 is a side elevational view of the lower portion of the clasp of FIG. 15.

FIG. 30 is a view similar to FIGS. 29 with the operating lever and jaws in the inoperative mode, and FIG. 31 is a side elevational view of the male and female terminals as they appear just prior to being connected together.

DETAILED DESCRIPTION OF THE INVENTION

Figure 1:
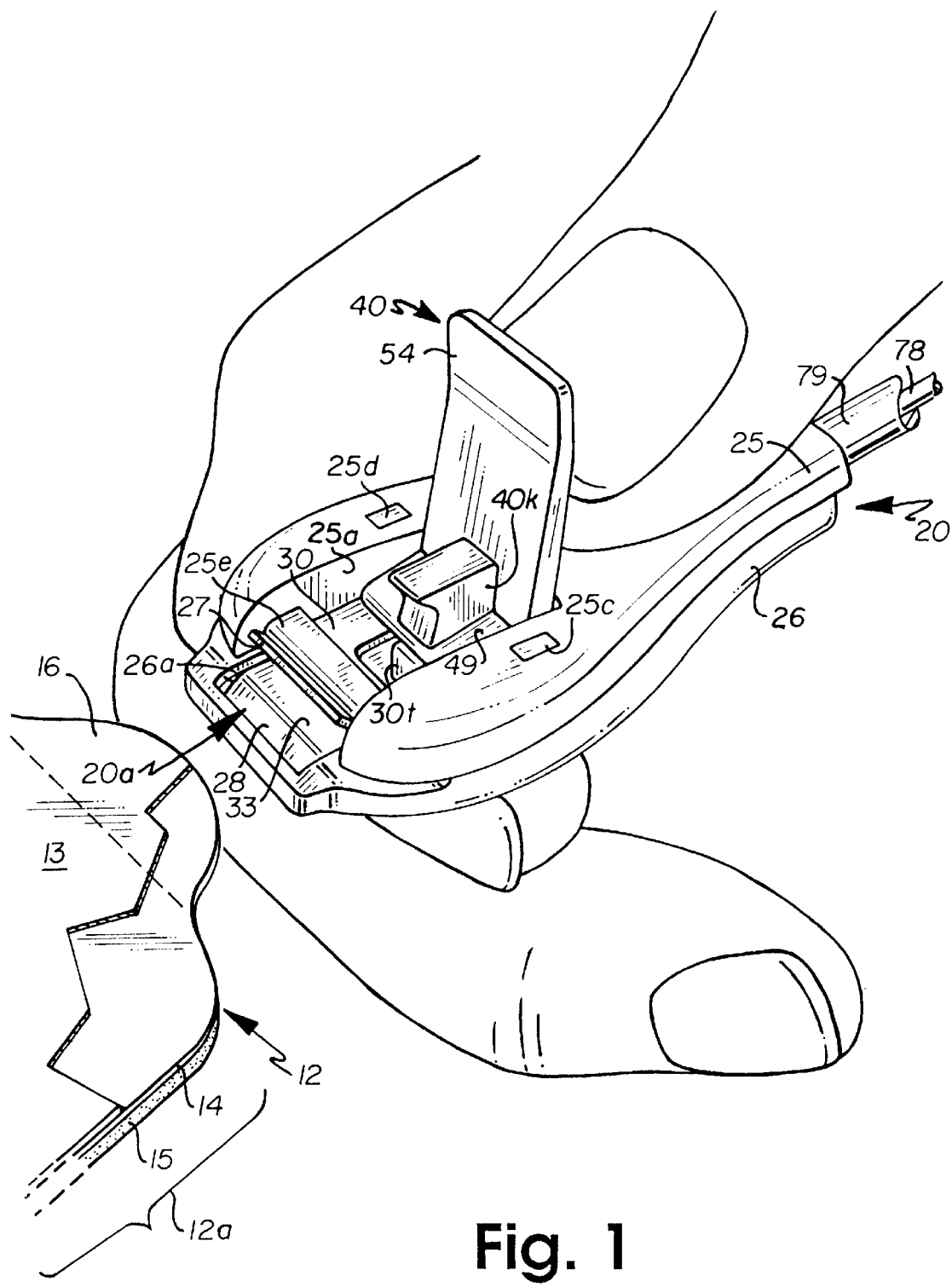
FIG. 1 is a perspective view of the new clasp just before the jaws are closed on a planar tab-type of external electrode which has been in general use.

In FIG. 1 a flexible, planar tab-type biomedical electrode sensor 12 is shown by way of example as a thin sheet of plastic 13 with a plated electrically conductive silver layer 14. The conductive layer 14 has a signal-sensing portion 12a and a signal transfer tab 16. On the lower surface of silver layer 14 is an electrically conductive hydrogel layer 15 which bonds to the skin of the patient and forms electrical contact therewith. The laterally extending signal transfer tab 16 is accessible for transfer of electrical signals sensed by the gel portion 15 which is in contact with the skin of the patient.

In the side and top views of the clasp connector of the present invention (FIGS. 4 and 5), a typical planar electrode 12 is shown with the signal transfer tab portion 16 in locking engagement with the present clasp structure indicated generally at 20a.

Figure 3:
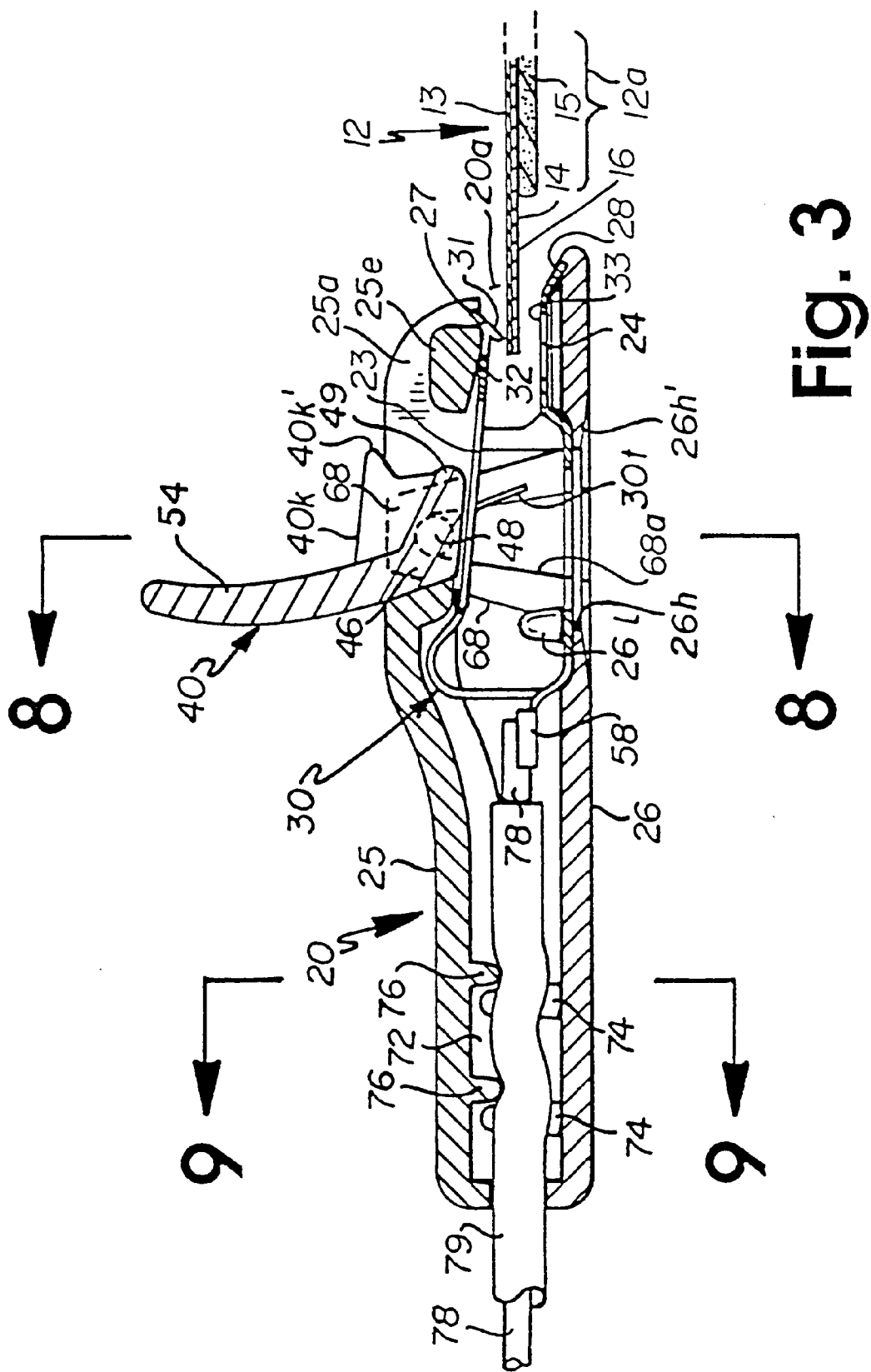
FIG. 3 is a vertical, longitudinal sectional view of a preferred embodiment of the present invention (substantially enlarged) with the jaws positioned in the non-operative open mode.

In FIGS. 1 and 3, an enlarged view of the clasp 20 is depicted in the non-operative mode, i.e., the clasp jaw opening 20a is not in clamping electrical contact with electrode 12. The clasp body 20 has a front orjaw end at the right and a rear end at the left as shown in the figures. Clasp 20 includes a flat leaf spring 30 with a pair of elongated arms 23 and 24 which serve as jaws, with aligned clasp surfaces presenting integral electrical contact surfaces 32, 33 confronting each other. The contact surfaces 32, 33 are normally biased by tie elasticity of spring 30 in an open spaced apart relationship as shown.

When the clip arms or jaws 23, 24 are biased in a spaced-apart posture, they will admit the insertion of the tab 16 of a biomedical electrode like 12 of FIG. 1. If desired, the inner electrical contact surfaces 32, 33 can be serrated for good electrical contact and mechanical gripping of inserted electrodes. Most preferably, the upper contact surface 32 is provided with a pair of laterally spaced, downwardly and inwardly projecting teeth or barbs 31 (FIGS. 3, 10 and 12–14) formed by making a V-shaped cut in the spring 30 for more reliably gripping the signal transfer tab 16.

The inner contact surfaces 32, 33 of the jaw portions of the clip arms 23, 24 are configured to grasp the signal transfer tab 16. This is accomplished by forcing the contact surfaces 32, 33 toward one another to provide a firm grip on the tab 16 of electrode 12.

Spring 30 is metallic for conductive purposes, preferably being of plated, annealed spring steel (1050° grade, heat treated to Rockwell 45 hardness) or stainless steel and is completely sterilizable upon disconnection from the electrode 12 between uses. The spring 30 has a gauge of 0.012"±0.00075" and is plated first with copper and then with laboratory grade nickel. As shown, the contact surfaces 32, 33 are well spaced apart until ready to clasp the electrode 12.

Affixed above the intermediate portion of upper clip arm 23 is a thumb-length jaw operating lever 40 which rotates forwardly on laterally extending aligned pivots 48 between a lever-up inoperative position (FIG. 3) and a lever-down operating position (FIG. 4) in line with the clasp body. In the latter position, the electrode 12 is gripped tightly between the contact surfaces 32, 33 of clip arms 23, 24. It should be noted that during the jaw closing operation, the free end 54 of lever 40 swings forwardly toward the jaw opening 20a. This permits it to be easily operated with the finger or thumb, tending to move the open clasp 20 toward engagement with the electrode 12 rather than away from it. This gives the clasp 20 superior closing characteristics from a human engineering standpoint.

Figure 4:
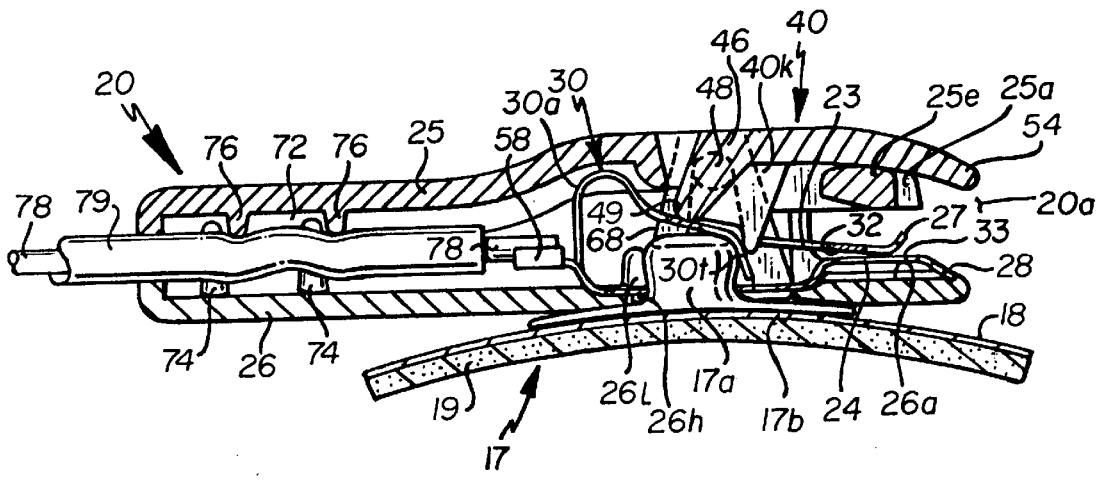
FIG. 4 is a vertical, longitudinal sectional view of the embodiment of FIG. 3, with the clasp in the operative mode, i.e., closed.
Figure 5:
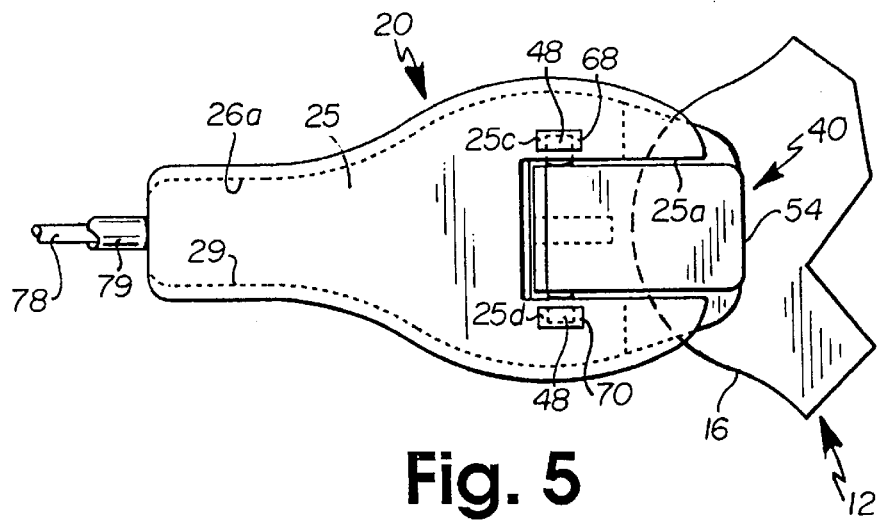
FIG. 5 is a top plan view of the clasp structure of FIG. 4 when in the operative mode.

The lower end 46 of lever 40 has a protrusion or cam 49 which engages the top of spring 30 (FIGS. 4 and 5). In the lever-up inoperative position of FIGS. 1 and 3, the protrusion 49 allows the contact surfaces 32, 33 of clip arms 23, 24 to be spaced apart. In the in-line or operating lever position, the cam 49 biases the upper portion 36 downwardly, clamping the contact surfaces 32, 33 of clip arms 23, 24 on the tab 16 as in FIG. 4.

When the clasp 20 is to be employed with electrodes already in place on a patient's body, and while the contact surfaces 32, 33 are still in the open posture, they are slipped over the electrode tab 16 and then closed with a finger or thumb by rotating lever 40 forwardly, i. e., toward free ends 27, 28 of the jaws and the electrode 12 itself, causing the protrusion 49 to compress the middle portion of spring 30 so as to move the upper arm 23 downwardly into locking closure on the electrode 12 (see FIG. 4). The electrode 12 is then secured against normal jostling or cable flexure, until the clasp 20 is purposefully released by prying lever 41 upwardly and rearwardly.

Figure 6:
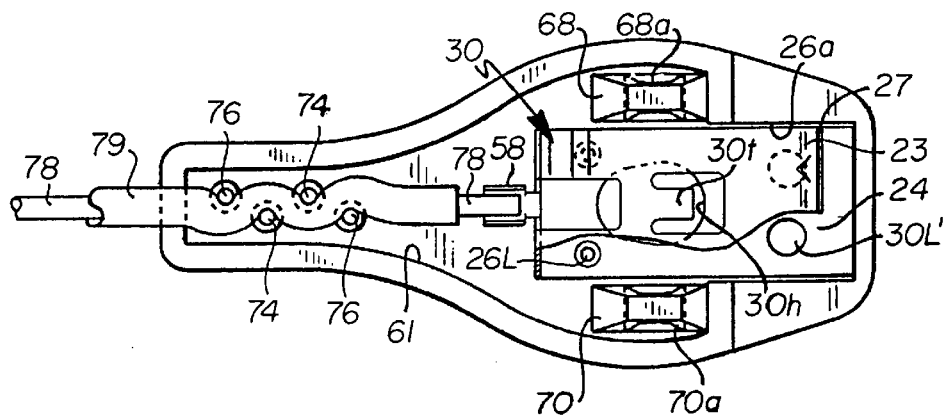
FIG. 6 is a plan view of the bottom portion of the clasp with the spring and lead wire installed.

In a preferred embodiment (FIG. 3), the spring 30 is generally U-shaped and has a closed end 30a as seen at the left in FIGS. 3 and 4. The clasp 20 includes an upper body portion 25 and a lower body portion 26. During assembly, the spring 30 is dropped onto the clasp lower body portion 26 and after assembly its free ends 27, 28 rest snugly against adjacent clasp inner pocket 26a (FIGS. 1 and 6). The closed portion, i.e., the left end 30a of the spring 30 is also provided with a centrally-positioned, rearwardly extending, rigid, trough-shaped, electrically conductive lug 58. An electrical lead 78 has its inner end contacting the surface of the lug 58 and is preferably soldered to it.

Figure 8:
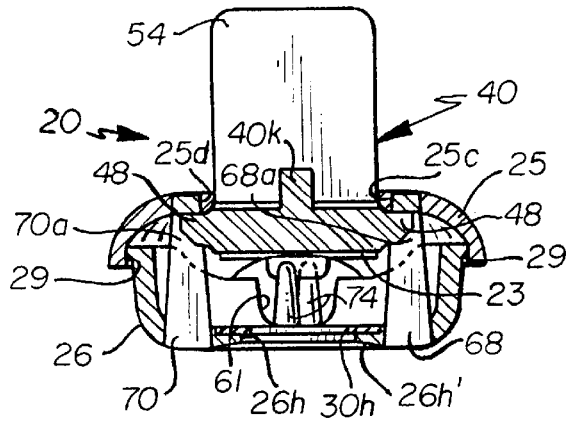
FIG. 8 is a vertical cross-sectional view taken on line 8—8 of FIG. 3.

The upper and lower portions 25 and 26 of the clasp 20 are of a molded material, preferably plastic resin which has electrical insulating properties, typically of nylon or polycarbonate plastic which is completely sterilizable. The upper portion 25 has a forwardly facing, upwardly opening, central cavity 25a to receive the lever 40 (FIG. 5). The lower portion 26 has an upwardly facing recess 26a aligned beneath it to receive the spring 30. On either side of the spring 30 are upwardly extending lever supporting posts 68, 70 which have laterally aligned central openings 68a, 70a to receive the pivots 48 of the lever 40 (FIG. 8). During assembly, the lever 40 is mounted by forcing the upper ends of the supporting posts 68, 70 apart slightly and then allowing them to snap back toward one another to enclose the pivots 48 of lever 40. The upper portion 25 of the clasp 20 is then forced downwardly onto the lower portion 26, causing the tops of the posts 68, 70 to enter openings 25c and 25d (FIG. 5) as a peripheral snap connection 29 (FIGS. 5, 8 and 9) locks the upper and lower portions 25, 26 together. The posts 68, 70 are then held permanently in the openings 25c, 25d which act as retaining means so that they can no longer be spread apart. The lever 40 will, therefore, resist being dislodged by a force many times the force required to separate snap connection 29. When the lever 40 is pivoted forwardly, the posts 68, 70 hold it securely in place. It is not the snap connection 29 which holds it since the entire load exerted by the lever 40 is carried by the posts 68, 70. This feature of the invention provided by the advantage of having the load carried by posts 68, 70 makes it possible to assemble the invention without the necessity of welds which reduces manufacturing costs. The posts 68, 70 will, in fact, hold a force applied to the lever 40 that is twenty times that which is needed to open the clasp 20 at the snap connection 29.

Figure 9:
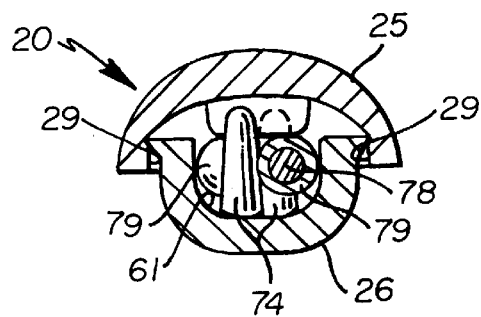
FIG. 9 is a vertical cross-sectional view taken on line 9—9 of FIG. 3.
Figure 10:
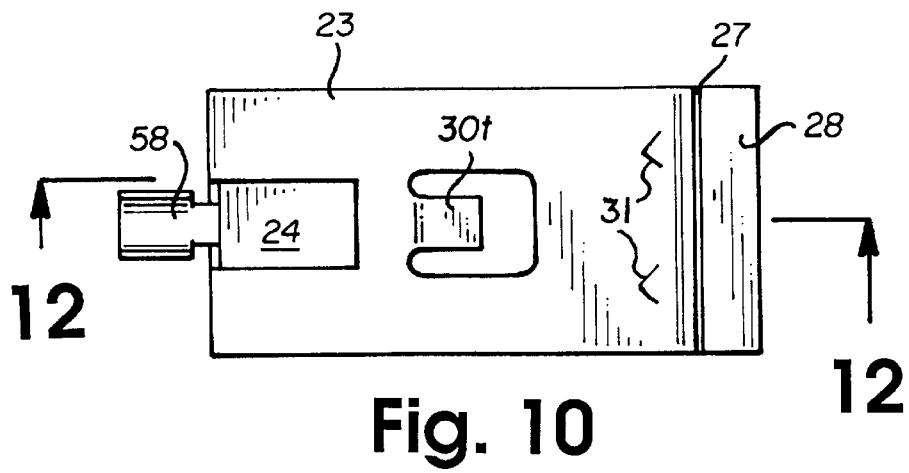
FIG. 10 is a plan view of the spring.
Figures 11, 12:
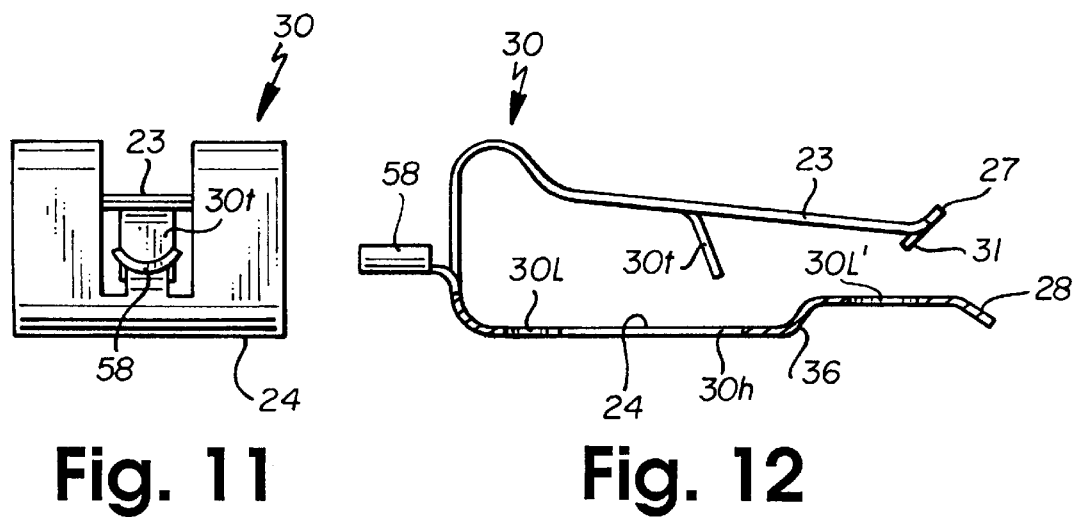
FIG. 11 is a left-end view of the spring.
FIG. 12 is a vertical cross-sectional view of the spring taken on line 12—12 of FIG. 10.
Figures 13, 14:
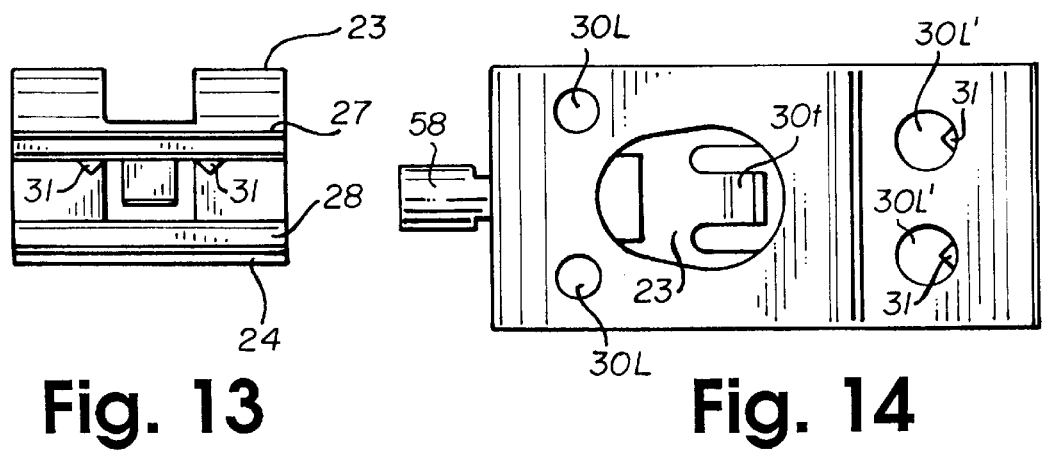
FIG. 13 is a right-end elevational view of the spring.
FIG. 14 is a bottom view of the spring.

An insulating sleeve 79 surrounds an insulated electrically conductive cable or lead 78 which is also connected at its distal end to a meter or other measuring means or source of current for stimulation (not shown). The lead 78, 79 is shown passing through a central opening 61 in the clasp 20 (FIGS. 6, 8 and 9). The vertical sectional views of FIGS. 8 and 9 show the clasp body 20 provided with a discrete U-shaped internal channel 61 therethrough, in which the inner terminal length of lead 78 rests. The lead 78, 79 is held in a serpentine passage between staggered pins including two upper retaining pins 76 and two lower retaining pins 74. The pins 74, 76 act as a maze which serves as a strain relief function and are fabricated as a part of the upper and lower portions 25, 26 of the clasp 20.

Figure 2:
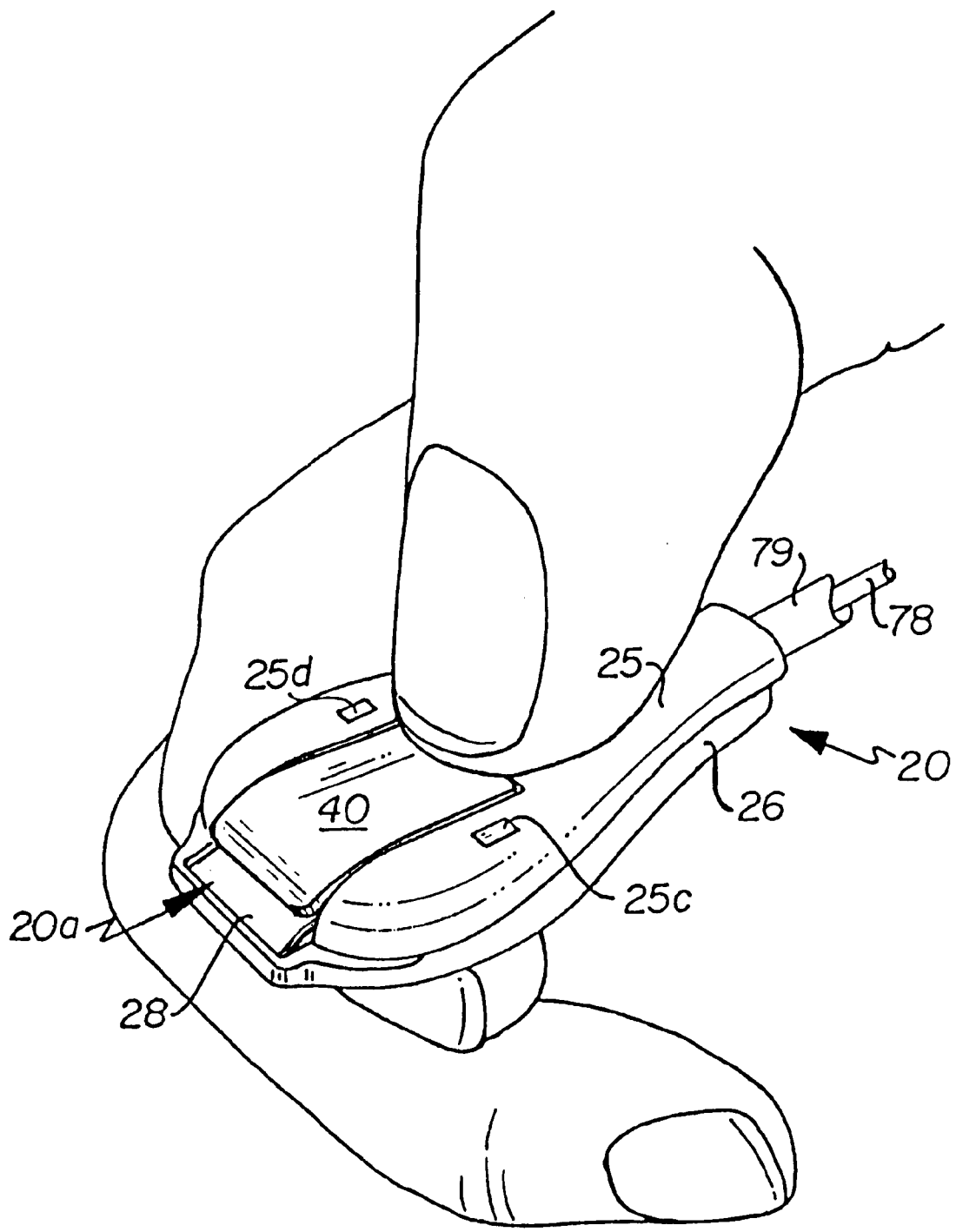
FIG. 2 is a view similar to FIG. 1 with the clasp jaws in the closed position.

The operative mode of the clasp 20 is depicted in FIGS. 2 and 4, in which a planar signal transfer tab 16 (FIG. 1) is firmly gripped between the contact surfaces 32, 33 of clip arms 23, 24. Lever 40 has been rotated forwardly to be in line with the longitudinal dimension of clasp 20, causing cam 49 to rotate clockwise as seen in FIG. 4 and bias downwardly the upper arm 36 of spring 30 to hold the jaws in clamping position.

The free length of lead 78, 79 is retained in operative contact by the crimping of retaining pins 74, 76 in the channel 61 and conductor 78 is soldered to lug 58 (FIG. 3).

To assemble the clasp 20, the conductor 78 is first soldered to lug 58. The lead 78, 79 is then threaded through channel 61 between the pins 74, 76. Lever 40 is then snapped into place on the posts 68, 70. The upper and lower outer insulator casing portions 25, 26 are then snapped together at 29 and the assembled clasp 20 with its coupled cable 78, 79 is ready for use.

In FIG. 5 is shown a top plan view of the clasp 20 with the lever 40 in the operating mode. In this mode the lever 40 is thrown forwardly into the upwardly opening cavity 25a which receives the free end 54 of the lever 40, providing a clasp that is free of projections and has a smoothly contoured surface. Extending laterally across the open end of the cavity 25a is a lever support bar 25e.

The feature of the invention used for holding a snap-type electrode will now be described in connection with FIGS. 4 and 7.

Figure 7:
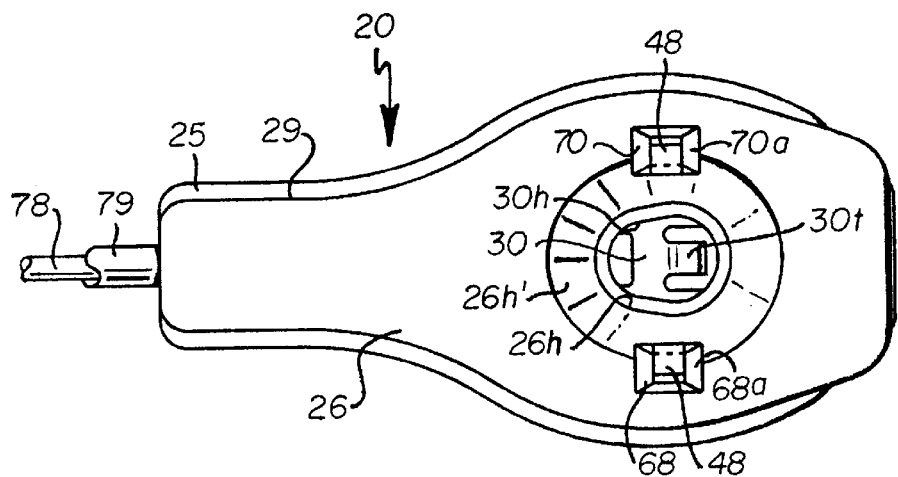
FIG. 7 is a bottom view of the invention.
Figure 7A:
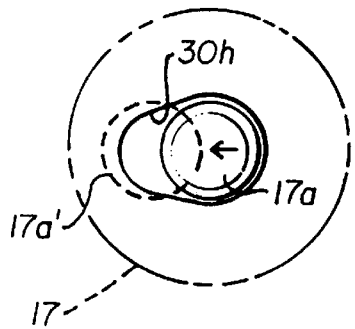
FIG. 7A is a bottom view of an opening in the bottom of the clasp as it appears when a stud of the snap-type electrode is inserted therein.

Near the center of the bottom portion 26 of the clasp 20 is an oblong opening 26h which is slightly larger at its forward end as shown in FIG. 7. Around the opening 26h is an upwardly and centrally tapered surface 26h'. Aligned above it is a similarly shaped opening 30h in the lower arm 24 of the spring 30. The spring 30 is also provided with two pairs of openings 30L and 30L' in the lower arm 24. The openings 30l are placed over aligned locating pins that project upwardly from the lower surface of the lower portion 26 of the clasp 20 for holding the spring 30 in place. The openings 30L' receive the barbs 31 when the jaws 20a are closed. The forward portion of the opening 26h and the forward portion of the opening 30h of the spring 30 are large enough to accommodate the stud 17a of a snap-type electrode 18 shown in FIG. 4. When the stud 17a is introduced into the forward enlarged end of the opening 30h in the spring 30 through opening 26h, it can do so because the opening is large enough at its forward end to accommodate the stud 17a. However, when the lever 40 is thrown forwardly and downwardly to the operating position, a keel 40k provided as an integral part of the lever 40 exerts a rearward force on a downwardly projecting tab or finger 30T which extends downwardly from the upper spring arm 23, causing tab 30T to be deflected rearwardly so as to shift the lug or stud 17a of the snap-type electrode 18 rearwardly in the oblong opening 30h, thereby locking it in place. The stud 17a is shown shifted rearwardly to its locked position at 17a' in the opening 30h in FIG. 7A. It will be noticed that the upper end of the stud 17a is slightly enlarged. This enlargement will prevent the stud 17a from being withdrawn once the locking tab 30T is deflected rearwardly by the downward pressure applied by the keel 40k (FIG. 4). The tab or finger 30T also acts as a means for establishing electrical contact with the stud 17a.

Because the clasp of the present invention will handle both a tab-type electrode (FIG. 1) or a snap-type electrode as shown in FIG. 4, the clasp of the present invention can be considered a universal clasp, i.e., it will handle both types of biomedical electrodes now in use. It is therefore is much more convenient and provides an additional safety factor since it is ready for use with either type of electrode now employed in hospitals and clinics.

The present invention is also adapted for use and reuse in a sterile environment. The clasp 20 can be repeatedly sterilized in a steam autoclave. The capability of sterilizing the entire clasp structure in a steam autoclave is an advantage which was not available with certain prior art structures because of the lead wire construction.

In practice, the spring 30 can be fabricated from low carbon, cold-rolled steel having a nominal thickness of about 0.012". The entire structure is coated by medical-grade plating with nickel, so that no portion of the clasp is subject to rusting. Preferably an initial copper flash coating is applied, followed by a coating of laboratory grade nickel. In the alternative, stainless steel is used with or without plating. A typical embodiment has an overall length of about 3.5 cm and a height of about 0.7 cm. The length of lever 40 is about 1.2 cm.

The forward movement of the lever 40 toward the jaw-end of the clasp 20 at the right in FIGS. 1–4 provides a surprising improvement over the prior art since the movement of the finger or thumb in closing the jaws automatically pushes the clasp 20 in the correct direction to move the jaws onto the tab 16 or, in the case of a snap, to move the lug 17 toward the back of the opening 26h. It was discovered that this provides a surprising advantage from a human engineering standpoint. It should also be noticed that the reverse movement of the lever 40 has the same effect with the clasp 20 is being disconnected from the electrode. That is to say, the lever action helps to move the clasp 20 away from the electrode 12. This is particularly important since the opening and closing of the clasp 20 is carried out with one hand as one hand holds the clasp with the lead wire 78, 79 extending away from the clasp 20 in a line parallel with a person's arm. Since everything is accomplished with one hand, human engineering advantages of the invention are particularly significant and beneficial.

Reference will now be made to a second embodiment of the invention (FIGS. 15–31), wherein the same numerals refer to corresponding parts already described with certain changes in dimensions and proportions apparent in the figures. The second embodiment has all the advantages of the embodiment of FIGS. 1–14 but includes several additional beneficial characteristics and advantages.

Figure 17:
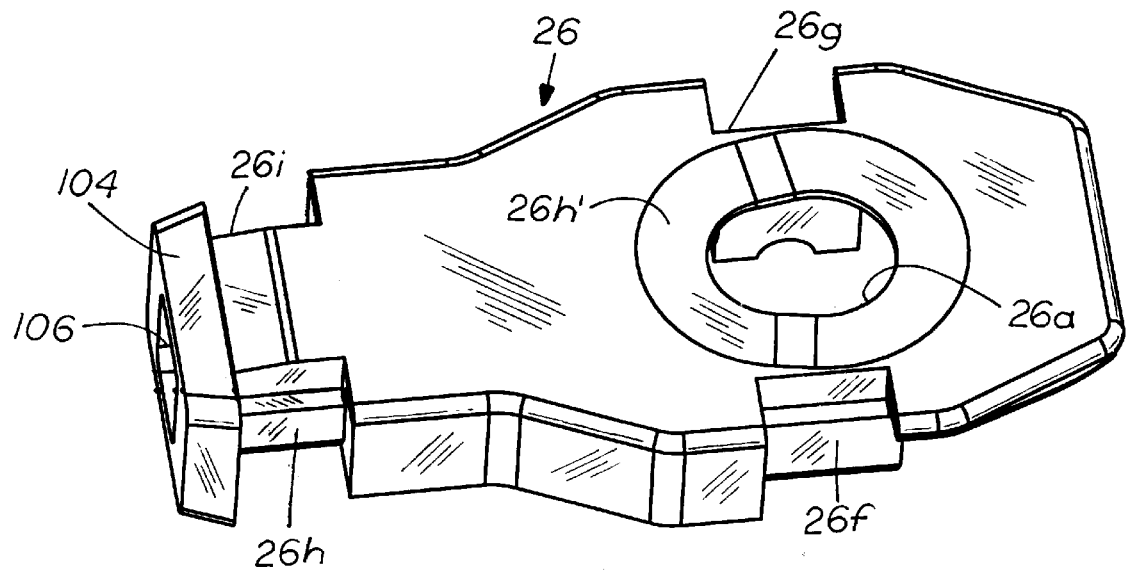
FIG. 17 is a bottom perspective view of FIG. 16.
Figure 18:
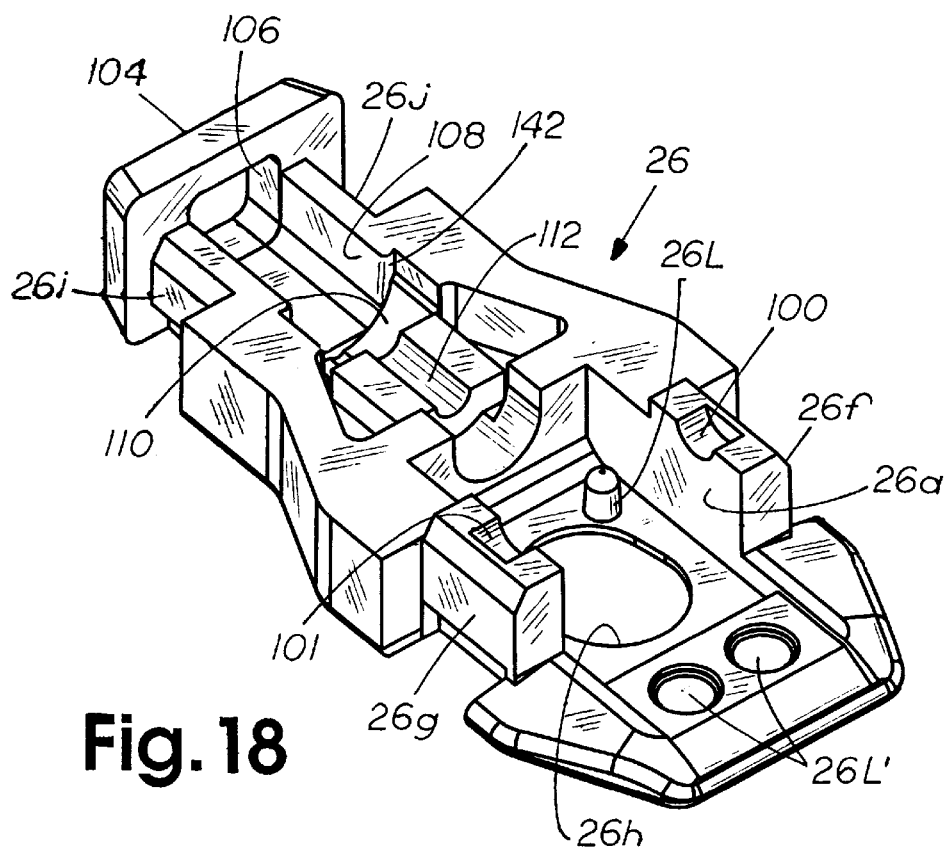
FIG. 18 is a top perspective view of the lower portion of the clasp of FIGS. 15–17.
Figure 19:
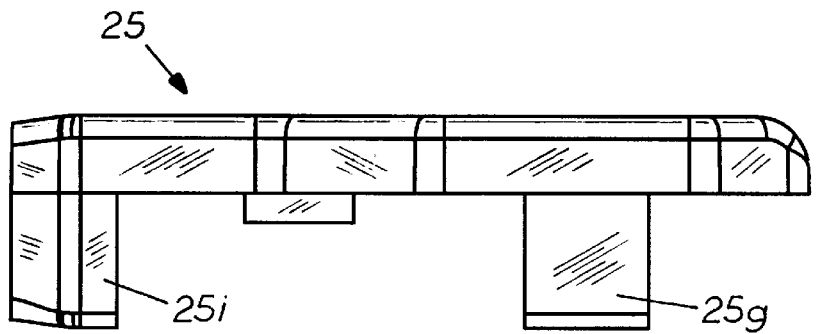
FIG. 19 is a side elevational view the upper portion of the clasp of FIG. 15.
Figure 20:
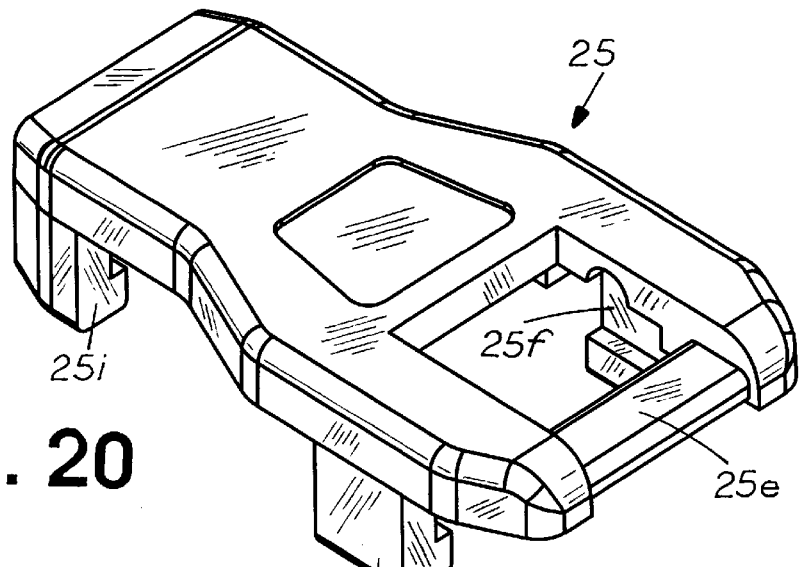
FIG. 20 is a perspective view of the upper portion of the clasp of FIGS. 15–19.
Figure 21:
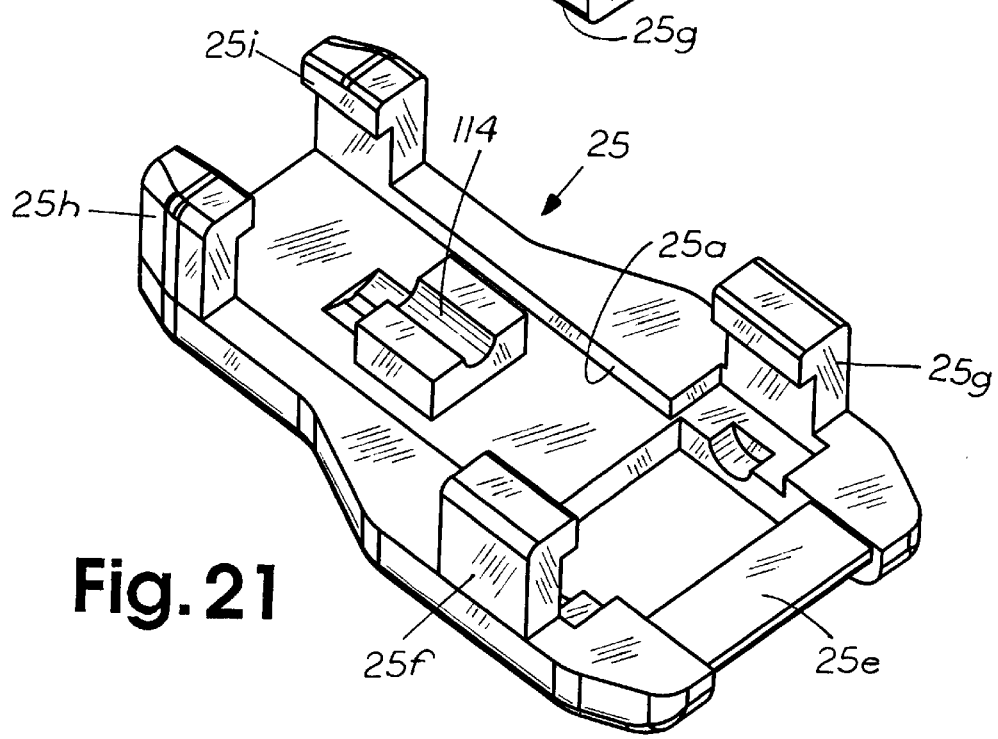
FIG. 21 is a top perspective view of the upper portion of the clasp of FIGS. 15–20.
Figure 22:
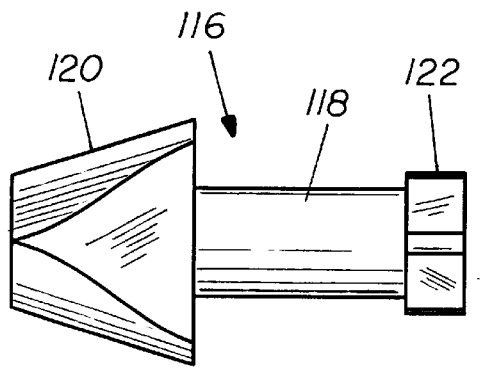
FIG. 22 is a side elevational view of the telescoping connector.
Figure 23:
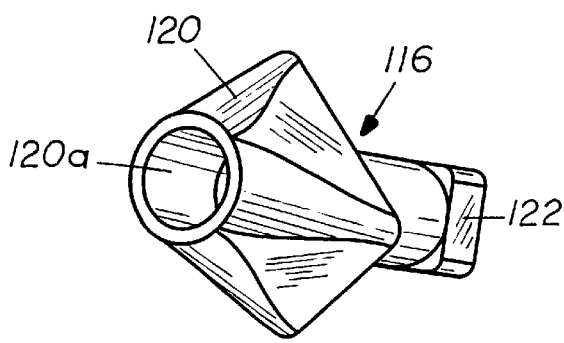
FIG. 23 is a rear perspective view of the connector of FIG. 22.
Figure 24:
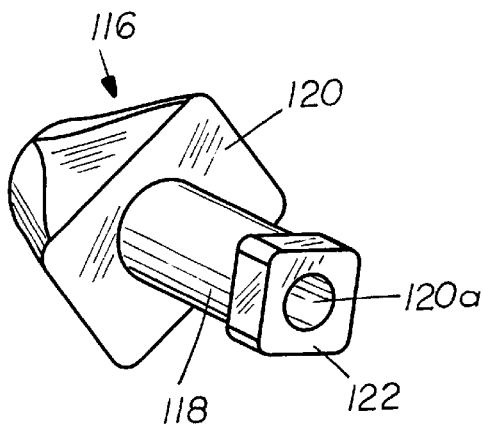
FIG. 24 is a front perspective view of the connector of FIGS. 22 and 23.
Figure 29:
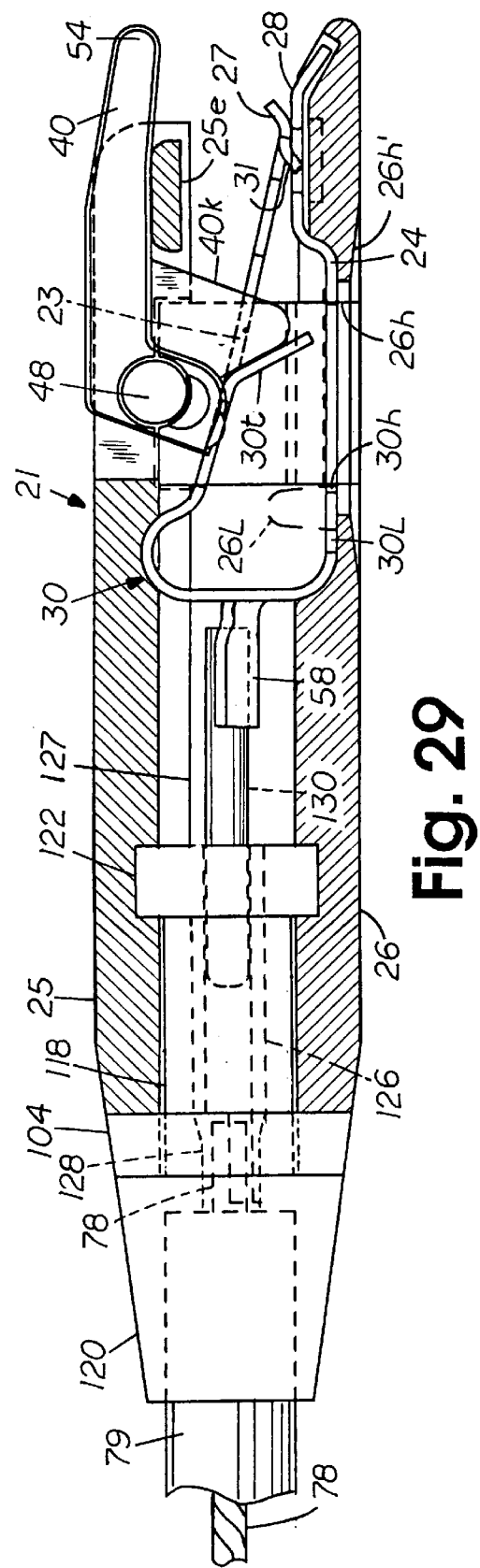
FIG. 29 is a longitudinal sectional view of the clasp taken on line 29—29 of FIG. 15 with the connector inserted.

The clasp body or housing 21 has a front orjaw end at the right in FIGS. 15, 29 and 30 and a rear end at the left as seen in these figures. The clasp 21 includes an upper portion 25 and a lower portion 26 which mate together along a longitudinally extending horizontal separation line 127. In this case, the posts 68 and 70 of the clasp 20 are replaced by longitudinally distributed (front to rear) connection means in the form of two longitudinally spaced pairs of downwardly extending lugs including two laterally spaced downwardly extending front lugs 25f and 25g and two downwardly extending laterally spaced rear lugs 25h and 25i (FIGS. 19–21) which are integral with the bottom portion 25 of the clasp housing 21. The upper and lower portions 25, 26 are preferably formed from a suitable plastic resin. The lugs 25f–25i are formed from the same plastic resin as the clasp 21 and are somewhat resilient. Each of the lugs 25f–25i includes a centrally extending catch or tang at its free end which, during assembly, provides a snap connection over the lower edge of corresponding slots 26f–26j in the lower portion 26 of the clasp 21 (FIGS. 16–18). Within the recess 26a in lower portion 26 of the clasp 20 is a pair of laterally spaced locating studs 26L (only one of which is shown in FIG. 18) near the rear of the recess 26a which extend into aligned locating holes 30L in the spring 30. At the front of the recess 26a is a pair of locating pockets 26L' (FIG. 18) which receive corresponding tabs 30L' (FIG. 30) in the spring 30 for holding the spring in place within the clasp 21.

To assemble the clasp 21, the spring 30 is placed in the recess 26a at the forward end of the lower portion 26 of the clasp 21 with the locating holes 30L of the spring 30 over the pins 26L, and the operating lever 40, which is provided with aligned laterally extending pivot pins 48, is placed within the lower journal halves 100 and 101 of a split bearing in the lower portion 26 which are aligned above the opening 26h. The top half of the split journal bearings 100, 101 for pivot pins 48 is shown at 103 in FIG. 21. To complete the assembly, the upper portion 25 of the clasp 21 is pressed downwardly onto the lower portion 26 so that the lugs 25f–25i enter the corresponding slots 26f–26j of the lower portion 26 of the clasp. As this is done, each catch at the end of each lug slides downwardly through the corresponding slots and then, when portions 25 and 26 are in the assembled position as shown in FIG. 15, the lower end of each lug snaps centrally to securely lock the upper and lower portions 25, 26 of the clasp 21 together. It will be noted that both front and rear ends of clasp portions 25, 26 are held together by the lugs. The lugs 25f–25i provide a very secure longitudinally distributed connection between the upper and lower portions 25, 26 of the clasp housing 21, in this way providing an even stronger and more reliable connection than in FIGS. 1–14 which will not come apart during use. The use of four lugs 25f–25i also makes it possible to provide a parting line 127 that is closer to a center line between the top and bottom surface of the clasp 21. Moreover, the operating lever 40 does not have to spread the posts 68, 70 apart as a separate assembly step and, accordingly, production is simplified. The possibility of weakening of the posts 68 and 70 by bending them is also avoided. The lugs adjacent the journals 100, 101, 103 for the operating lever 40 will prevent pressure exerted on the lever from separating the upper and lower portions of the clasp. Finally, precise positioning and secure retention of the telescoping connector to be described below is assured by the presence of the rear lugs 25h and 25i.

Refer now to FIGS. 16–18. It can be seen that at the rear of the lower portion 26 of the clasp housing 21 is an integral, vertically oriented end plate 104 of generally rectangular outline having a rectangular center opening 106 aligned with a longitudinally extending, upwardly opening slot 108 that terminates forwardly in a somewhat larger aligned opening 110, both of which are aligned with a groove 112 in lower portion 26. A cooperating aligned, downwardly facing groove 114 is provided in the upper portion 25.

Figure 25:
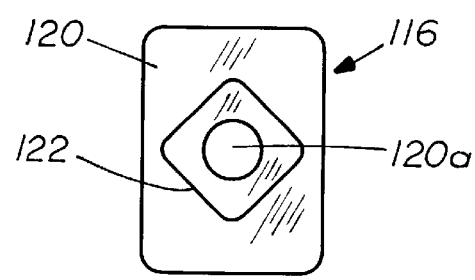
FIG. 25 is a front elevational view of the connector of FIGS. 22–24.
Figure 26:
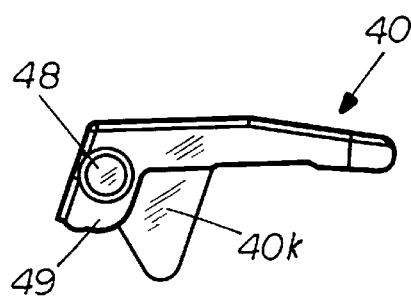
FIG. 26 is a side elevational view of the operating lever of the embodiment of FIG. 15.
Figure 27:
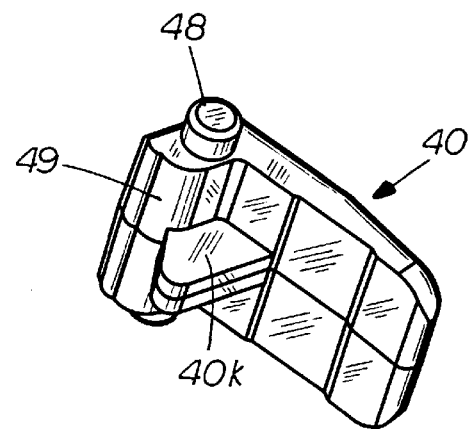
FIG. 27 is a bottom perspective view of the operating lever of FIGS. 15 and 26.
Figure 28:
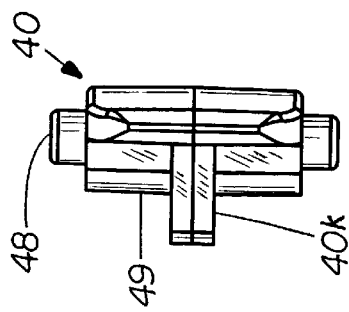
FIG. 28 is a front elevational view of the operating lever.

The electrically conductive lead wire 78 which is encased in insulation 79 terminates in a telescoping connector 116 that can be formed, preferably, from plastic resin and includes a central sleeve portion 118 having a round cross-section and enlarged terminal portions 120, 122 which have polygonal outlines (in this case rectangular) that are offset from one another about a longitudinal axis by an angle of 45° (FIG. 25). Extending longitudinally through the connector 116 is a central bore 120a which receives the end of the lead wire and the insulation 79 at its left end. Within the right end of the bore 120a is housed a tubular female receptacle 126 which can be secured to the inside of the bore 120a by adhesive, by means of an interference fit, or other suitable means. The tubular female electrical connector or terminal 126 is formed from metal and is secured by means of swaged connection 128 to the lead wire 78. FIG. 31 shows the electrically conductive lug 58 of the spring 30 which is attached, e.g., by spot welding, to a male terminal or pin 130 which slides into the central passage 126a of the female terminal 126 when the connector 116 is inserted into the clasp 21. The end of the pin 130 adjacent the spring 30 is held securely in place between the grooves 112, 114.

The passage 106, 108 has a rectangular cross-sectional configuration of just the appropriate size to accommodate the terminal portion 122 of the connector 116. However, after the terminal portion 122 has entered the larger opening 110, the person inserting the connector 116 can give the connector 116 a 45-degree turn in a clockwise direction as shown by arrow 140 in FIG. 15, thereby aligning the rectangular edge of terminal portion 120 with the rectangular end plate 104 and the adjacent rectangular surface of the clasp 21 so that the surface of connector 116 conforms to the surface of the clasp 21 as shown in FIG. 15. This lets the user know that the parts are properly connected.

To securely hold the telescoping connector 116 in place in its inserted position, one or more points or studs 142 (FIG. 18) can be provided in the opening 110 to engage and provide a snap-fit for locking the terminal portion 122 in the desired position of FIG. 15 after the connector 116 has been turned through a 45-degree arc 140. This aligns the surface of the terminal portion 120 and the adjacent surface of the clasp 21. Alignment of these two surfaces enables the user to know when the connector 116 is fully inserted so there is no mistake about how much the connector should be rotated to reach the installed position of FIG. 15. Removal of the connector 116 allows the clasp 21 or lead wire 78 to be replaced if damaged.

The connector 116 is very easy for the user to attach to the clasp 21 and yet provides a very secure mechanical and electrical connection between the lead wire 78 and the electrically conductive spring 30 and the electrical contacts defined by the jaws 23 and 24. In addition, the studs 142 will serve to reliably lock the connector 116 in place with a snap or click after it has been rotated to the correct position. The studs 142 also keep the surface of the rear portion 120 of the connector 116 aligned with the adjacent rear surface portion of the clasp 21. The telescoping connector 116 will hold the lead wires 78, 79 securely in place but enables the latter to be easily changed when necessary. The action of the jaws 23 and 24, the spring 30, and the action of the operating lever 40 in opening and closing the jaws 23 and 24 and in retaining an electrode stud 17a in the opening 26h is substantially the same as described in connection with the clasp 20 (FIGS. 1–14).

The spring 30 can be formed from metal or, if desired, the entire spring 30 including the jaw portions 27, 28 can be formed from any suitable, commercially available, electrically conductive, non-metallic plastic resin such as a composite thermoplastic material, e.g., polycarbonate resin containing a conductive substance such as carbon or an electrically conductive resin or any other suitable electrically conductive plastic resin known in the art. If resin is used, the thickness of the spring 30 will normally be increased to provide the appropriate strength and the pin 130 is preferably made integral with the spring 30, both components being formed in a die as one piece, e.g., by plastic injection molding. The non-metallic plastic spring 30 and pin 130, although capable of reliably carrying current to and from the biomedical electrode 12, are transparent to x-rays and allow continuous monitoring in an MRI examination. Accordingly, an x-ray film will show all the anatomical details of the patient without being obstructed as it would be if metal components were used. This makes it possible for a physician to interpret x-rays with greater precision.

Many variations of the present invention within the scope of the appended claims will be apparent to those skilled in the art once the principles described herein are understood.

What is claimed is:

1. A universal clasp structure for establishing electrical connection to either a) a tab-style medical electrode with a lateral tab on an edge thereof or b) a snap-style electrode having stud projecting upwardly from a top surface thereof, said clasp structure comprising,
    a pair of opposed and aligned cooperating jaws that move apart or together for grasping a tab portion of an electrode placed therebetween when the jaws are engaged in a closed position for establishing electrical contact with the tab,
    said clasp structure having a member with an opening therein that extends from an outer surface thereof to an inner portion thereof and the opening is sized to receive a stud of a snap-style medical electrode, and
    an electrical conductor formed from electrically conductive plastic material is positioned interiorally of the opening for establishing electrical contact with the stud when the stud is positioned to extend through the opening.

2. The clasp of claim 1 wherein the conductor formed from electrically conductive plastic material is a generally U-shaped resilient member wherein one of said jaws comprises an upper jaw at a top end thereof, and another of said jaws comprises a lower jaw at a bottom end thereof and said member has an electrically conductive terminal for establishing an electrical connection with a lead wire to carrying current to or from the clasp structure.

3. The apparatus of claim 2 wherein a conductive portion of the electrically conductive terminal is a pin, and the lead wire has connected thereto an electrically conductive sleeve adapted to slide telescopically over the pin for establishing an electrical connection between the terminal and the lead wire.

4. The apparatus of claim 2 wherein a connector is attached to a free end of the lead wire, said connector has an end portion at a free end thereof adapted to be slid into the clasp structure through a passage therein, the clasp has a slot to receive the end portion and for permitting the connector to be rotated about a longitudinal axis of the connector after the end portion thereof has entered the slot to thereby locate the connector in an installed position within the clasp.

5. The apparatus of claim 4 wherein the connector has an outer end portion that is aligned with adjacent exterior walls of the clasp when the connector has been rotated on its central longitudinal axis to said installed position.

6. A clasp structure capable of being releasably secured to a planar tab-type contact of a biomedical monitoring or stimulating electrode for carrying current to or from the body of a patient comprising,
    a) a clasp body having a front end and an outwardly opening connector-receiving passage,
    b) a pair of opposed cooperating jaw members at the front end of the clasp body with a jaw opening therebetween,
    c) at least one jaw member having an electrical contact at a free end thereof and the jaw members being aligned in opposed relationship confronting each other at the front end of the clasp, d) a resilient spring means operatively supported by the clasp body and associated with the jaw members for biasing the jaw members toward an open position wherein the jaw members are spaced apart from one another, e) an operating lever movably mounted as a part of the clasp structure and operatively associated with the jaw members, said lever having an exposed portion to which pressure can be applied with a finger or the thumb for closing the clasp, f) said lever is movably supported on the clasp body and has a jaw-actuating portion operatively associated with at least one of the jaws, g) a terminal electrically connected to the electrical contact, and h) a removable connector member, said removable connector being sized to be slid into the passage within the clasp structure, said connector having a electrically conductive member adapted for contacting the terminal when the removable connector is inserted into the passage within the clasp body.

7. The clasp structure of claim 6 wherein the connector has an inner end portion at a free end thereof, the clasp has a slot to receive the end portion of the connector and to permit the connector to be rotated about a central longitudinal axis thereof after the inner end portion has entered the slot for locating the connector in an installed position within the clasp structure.

8. The clasp structure of claim 7 wherein the connector has an outer end portion, both end portions have a predetermined outline and at least said outer end portion of the connector is polygonal in outline, said polygonal outline is offset from the outline of the inner end portion about the central longitudinal axis of the connector by a predetermined angular offset, and said installed position is reached when the rectangular outline of the outer portion of the connector is aligned with an adjacent surface portion of the clasp structure.

9. The clasp structure of claim 8 wherein the polygonal outline of the outer end portion is rectangular.

10. A biomedical clasp for establishing electrical contact with a patient-contacting electrode comprising, a clasp structure having a front end and a rear end and being adapted to be connected to a stud of a biomedical electrode, an operating lever mounted on the clasp structure for movement relative thereto for causing the biomedical electrode to be held by the clasp, the clasp structure includes an upper body housing portion and a lower body housing portion, the upper and lower body housing portions are connected together by longitudinally distributed connecting members that extend between said upper and lower body portions of the clasp structure for securing the upper and lower portions to one another, the operating lever is journaled between said upper and lower body portions for pivotal movement, and at least some of the connecting members are positioned proximate the journals for the operating lever.

11. The clasp structure of claim 10 wherein the longitudinally distributed connecting members comprise a pair of laterally spaced apart lugs located proximate the journals of the operating lever and a second pair of laterally spaced apart lugs located proximate the rear end of the clasp structure, and each of the lugs has a catch at the free end thereof for engaging a mating portion of the clasp structure to hold together the upper and lower portions thereof.

12. The clasp structure of claim 11 wherein the lugs comprise four extensions that are integral with the upper portion of the clasp structure and project downwardly from the upper portion of the clasp structure for engaging said lower portion thereof.

13. A clasp structure for establishing electrical connection to a medical electrode, said clasp structure comprising, a clasp body having a front end, a longitudinally extending sliding connection for a removable connector, and said clasp structure including a pair of opposed cooperating jaws at the front end of the clasp body that move apart or together for grasping the electrode when placed therebetween to establish electrical contact with the electrode, a terminal supported by the clasp body for establishing an electrical connection to the electrode, a removable connector member, said removable connector member being sized to provide a sliding connection with the connector on the clasp body and rotated to an installed position, said connector member having an electrically conductive member adapted to contact the terminal when the connector member is in contact with the connector on the clasp body, the connector member has an outer end portion, said outer end portion of the connector has a multiple-sided outline, and said installed position is reached when the multiple-sided outline of the outer portion of the connector is aligned with an adjacent surface portion of the clasp body.

14. The clasp structure of claim 13 wherein the multiple-sided outline is rectangular.

15. The clasp structure of claim 13 wherein the connector member has an inner end portion and the inner end portion engages a locking member within the clasp body for holding the connector member therein when in the installed position.

16. A biomedical clasp structure for establishing electrical contact with a patient-contacting electrode comprising, a clasp body defining a housing, said clasp body having a receptacle for receiving a stud of the patientcontacting biomedical electrode, an operating lever mounted on the clasp body for movement relative thereto for causing the biomedical electrode to be held by the clasp body, the clasp body includes first and second adjacent body housing portions, and two spaced apart pairs of lugs, each pair of lugs being supported by the clasp body, each lug of each pair being spaced apart from the other lug of the same pair, and each lug having a member thereon for connecting the lug to an adjacent body housing portion to hold the clasp structure together.

17. The clasp structure of claim 16 wherein the member on the lug comprises a catch proximate the free end of each lug for engaging a the adjacent body housing portion of the clasp body to hold the first and second portions of the clasp body together.

* * * * *

UNITED STATES PATENT AND TRADEMARK OFFICE
CERTIFICATE OF CORRECTION

PATENT NO. : 5,944,562
DATED : Aug. 31, 1999
INVENTOR(S) : CHRISTENSSON, Eddy K.G.

It is certified that error appears in the above-indentified patent and that said Letters Patent is hereby corrected as shown below:

Claim 13 (Col. 12, line 23) before "connector" and after "with", change "the" to ---a---.

Claim 13 (Col. 12, lines 13, 31 and 34), after "connector" insert ---member---.

Signed and Sealed this

Fourth Day of July, 2000

Attest:

Q. TODD DICKINSON

Attesting Officer

Director of Patents and Trademarks